United States Patent [19]

Hsu

[11] Patent Number: 5,653,996
[45] Date of Patent: Aug. 5, 1997

[54] METHOD FOR PREPARING LIPOSOMES

[75] Inventor: Chung C. Hsu, Los Altos Hills, Calif.

[73] Assignee: Genentech, Inc., South San Francisco, Calif.

[21] Appl. No.: 407,424

[22] Filed: Mar. 17, 1995

Related U.S. Application Data

[63] Continuation of Ser. No. 84,933, Jun. 30, 1993, abandoned.

[51] Int. Cl.$^6$ .................................................. A61K 9/127
[52] U.S. Cl. ............................ 424/450; 264/4.1; 264/4.3
[58] Field of Search .......................... 424/450; 264/4.1, 264/4.3

[56] References Cited

U.S. PATENT DOCUMENTS

| | | |
|---|---|---|
| 3,773,919 | 11/1973 | Boswell . |
| 4,301,968 | 11/1981 | Berger et al. . |
| 4,337,896 | 7/1982 | Berger et al. . |
| 4,452,747 | 6/1984 | Gersonde . |
| 4,508,703 | 4/1985 | Redziniak . |
| 4,743,449 | 5/1988 | Yoshida . |
| 4,753,788 | 6/1988 | Gamble . |
| 4,776,991 | 10/1988 | Farmer . |
| 4,781,871 | 11/1988 | West . |
| 4,830,858 | 5/1989 | Payne . |
| 4,895,452 | 1/1990 | Yiournas . |
| 4,895,719 | 1/1990 | Radhakrishnan . |
| 4,897,355 | 1/1990 | Eppstein . |
| 4,921,757 | 5/1990 | Wheatly . |
| 4,946,787 | 8/1990 | Eppstein . |
| 4,957,735 | 9/1990 | Huang . |
| 4,971,802 | 11/1990 | Tarcsay . |
| 4,973,465 | 11/1990 | Baurain . |
| 5,019,400 | 5/1991 | Gombotz . |
| 5,077,057 | 12/1991 | Szoka .............................. 424/450 |
| 5,188,838 | 2/1993 | Deleuil . |
| 5,192,528 | 3/1993 | Radhakrishnan . |

FOREIGN PATENT DOCUMENTS

| | | |
|---|---|---|
| 48713/85 | 4/1986 | Australia . |
| 058481 | 8/1982 | European Pat. Off. . |
| 172007 | 2/1986 | European Pat. Off. . |
| 190926 | 8/1986 | European Pat. Off. . |
| 267050 | 11/1988 | European Pat. Off. . |
| 335133 | 4/1989 | European Pat. Off. . |
| 357773 | 3/1990 | European Pat. Off. . |
| 2145107 | 3/1985 | United Kingdom . |
| WO86/01714 | 3/1986 | WIPO . |
| WO87/07502 | 12/1987 | WIPO . |
| WO88/01864 | 3/1988 | WIPO . |
| 89/11850 | 12/1989 | WIPO . |
| 90/13285 | 11/1990 | WIPO . |
| 90/14074 | 11/1990 | WIPO . |
| 92/03123 | 3/1992 | WIPO . |

OTHER PUBLICATIONS

Batzri et al., "Single bilayer liposomes prepared without sonication" *Biochimica et Biophysica Acta* 298:1015–1019 (1973).

Enhorning et al., "Prevention of neonatal respiratory distress syndrome by tracheal instillation of surfactant: a randomized clinical trial" *Pediatrics* 76(2):145–153 (1985).

Farr et al., "Assessing the potential of aerosol–generated liposomes from pressurized pack formulations" *J. Controlled Release* 5:119–127 (1987).

Floros et al., "Isolation and characterization of cDNA clones for the 35–kDa pulmonary surfactant–associated protein" *Journal of Biological Chemistry* 261:9029–9033 (1986).

Fujiwara et al., "Pulmonary surfactant phospholids from turkey lung:comparison with rabbit lung" *Am. J. Physiol.* 218:218–225 (1970).

(List continued on next page.)

*Primary Examiner*—Gollamudi S. Kishore
*Attorney, Agent, or Firm*—Wendy M. Lee

[57] ABSTRACT

Methods are provided for the preparation of liposomes utilizing aerosolization of a solution comprising bilayer-forming materials and optional additional molecules onto an aqueous surface, the aerosolization being mist spraying through a frequency-generated vibrating nozzle.

28 Claims, 1 Drawing Sheet

OTHER PUBLICATIONS

Glasser et al., "cDNA and deduced amino acid sequence of human pulmonary surfactant–associated proteolipid SPL (Phe)" *Proc. Natl. Acad. Sci. USA* 84:4007–4011 (1987).

Glasser et al., "cDNA, deduced polypeptide structure and chromosomal assignment of human pulmonary surfactant proteolipid, SPL(pVal)" *Journal of Biological Chemistry* 263:9–12 (1988).

Glasser et al., "Two SP–C genes encoding human pulmonary surfactant proteolipid" *Journal of Biological Chemistry* 263:10326–10331 (1988).

Halliday et al., "Controlled trial of artificial surfactant to prevent respiratory distress syndrome" *Lancet* 1:476–478 (1984).

Hawgood et al., "Nucleotide and amino acid sequences of pulmonary surfactant protein SP 18 and evidence for cooperation between SP 18 and SP 28–36 in surfactant lipid adsorption" *Proc. Natl. Acad. Sci. USA* 84:66–70 (1987).

Jacobs et al., "Isolation of a cDNA clone encoding a high molecular weight precursor to a 6–kDa pulmonary surfactant–associated protein" *Journal of Biological Chemistry* 262(20):9808–9810 (1987).

Jobe et al., "Surfactant treatment: experimental basis for clinical use" *Am. Rev. Resp. Dis.* 136:1032–1033 (1987).

Kasahara et al., "Reconstitution and purification of the D–Glucose transporter from human erythrocytes" *Journal of Biological Chemistry* 252:7384–7390 (1977).

Kwong et al., "Double–blind clinical trial of calf lung surfactant extract for the prevention of hyaline membrane disease in extremely premature infants" *Pediatrics* 76(4):585–592 (1985).

Langer, "Controlled release of macromolecules" *Chem. Tech.* 12:98–105 (1982).

Langer et al., "Biocompatibility of polymeric delivery systems for macromolecules" *J. Biomed. Mater. Res.* 15:267–277 (1981).

Merritt et al., "Prophylactic treatment of very premature infants with human surfactant" *New England J. of Medicine* 315(13):787–790 (1986).

Ohsawa et al., "A novel method for preparing a liposome with a high capacity to encapsulate proteinous drugs: freeze– drying method" *Chem. Pharm. Bull.* 32:2442–2445 (1984).

Papahadjopoulos et al., "Sterically stabilized liposomes: improvements in pharmacokinetics and antitumor therapeutic efficacy" *Proc. Natl. Acad. Sci. USA* 88:11460–11464 (1991).

Pick, Uri, "Liposomes with a large trapping capacity prepared by freezing and thawing of sonicated phospholipid mixtures" *Archives of Biochemistry and Biophysics* 212(1):186–194 (1981).

Revak et al., "Use of human surfactant low molecular weight apoproteins in the reconstitution of surfactant biologic activity" *J. Clin. Invest.* 81:826–833 (1997).

Sidman et al., "Controlled release of macromolecules and pharmaceuticals from synthetic polypeptides based on glutamic acid" *Biopolymers* 22(1):547–556 (1985).

Stryer, Lubert, "Part II: Protein Conformation, Dynamics and Function" *Biochemistry*, New York:Freeman &Co. pp. 290–291 (1988).

Szoka, Jr. et al., "Comparative properties and methods of preparation of lipid vesicles (liposomes)" *Ann. Rev. Biophys. Bioeng.* 9:467–508 (1980).

Szoka, Jr. et al., "Procedure for preparation of liposomes with large internal aqueous space and high capture by reverse–phase evaporation" *Proc. Natl. Acad. Sci. USA* 75:4191–4199 (1978).

Usa, Chikashi, "Manufacture of liposomes for pharmacological and biochemical studies without use of volatile organic solvents" *Chemical Abstracts* 110(415):219082b, 1989.

Vitetta et al., "Redesigning nature's poisons to create anti–tumor reagents" *Science* 238:1098–1104 (1987).

Warr et al., "Low molecular weight human pulmonary surfactant protein (SP5): isolation, characterization, and cDNA and amino acid sequences" *Proc. Natl. Acad. Sci. USA* 84:7915–7919 (1987).

White et al., "Isolation and characterization of the human pulmonary surfactant apoprotein gene" *Nature* 317:361–363 (1985).

Whitsett et al., "Characteristics of human surfactant–associated glycoproteins A" *Pediatr. Res.* 19:501–508 (1985).

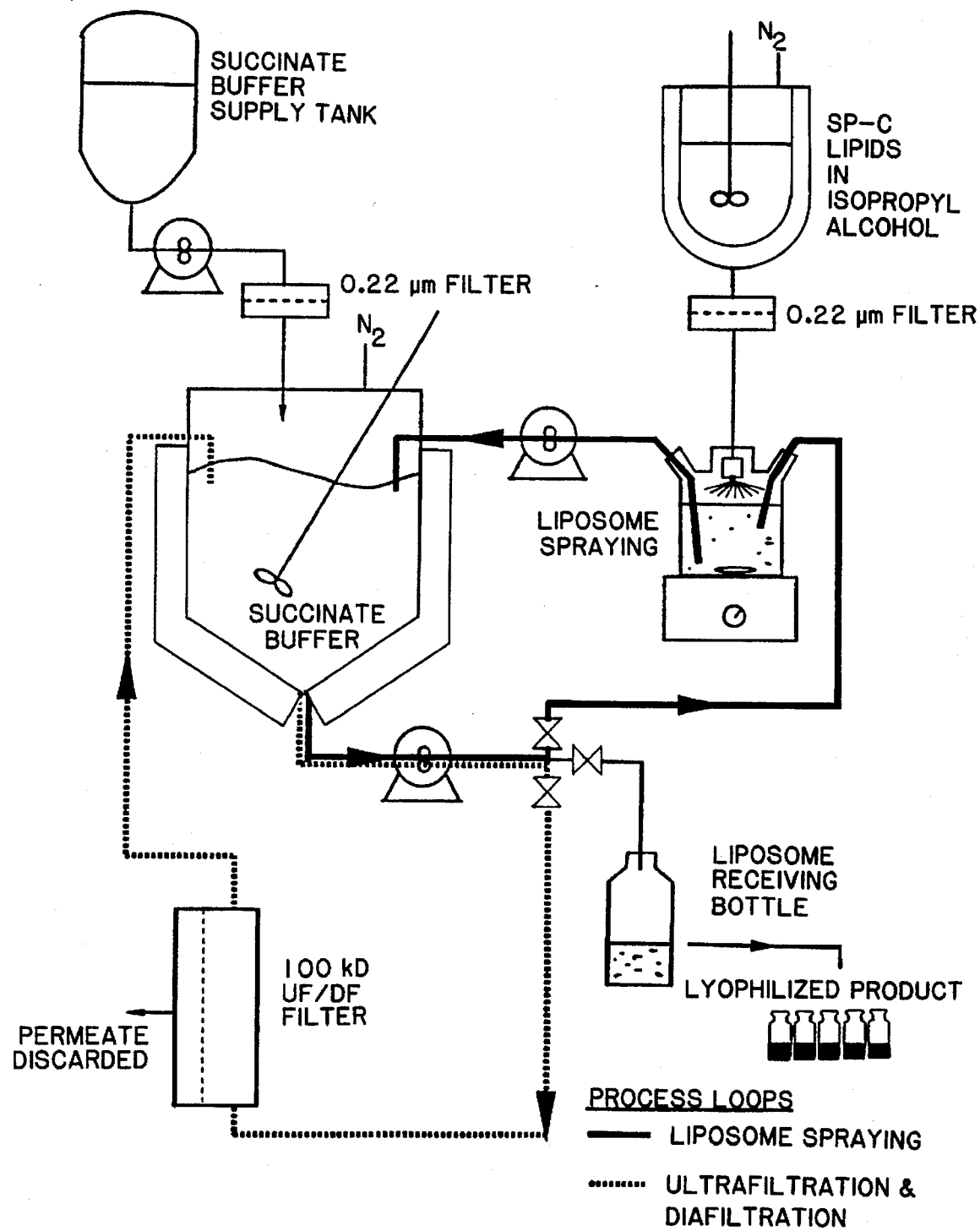

METHOD FOR PREPARING LIPOSOMES

This is a continuation of application Ser. No. 08/084,933 filed on 30 Jun. 1993, now abandoned, which application is incorporated herein by reference and to which application priority is claimed under 35 USC §120.

BACKGROUND OF THE INVENTION

I. Field of the Invention

The present invention is directed to methods of making liposomes, and the preparation of liposomes suitable for particular applications.

II. Description of Background and Related Art

Liposomes are small, spherical vesicles composed primarily of various types of lipids, phospholipids and secondary lipophilic components. These components are normally arranged in a bilayer formation, similar to the lipid arrangement of biological membranes. Typically, the polar end of a component lipid or lipid-like molecule is in contact with the surrounding solution, usually aqueous solution, while the non-polar, hydrophobic end of the lipid or lipid-like molecule is in contact with the non-polar, hydrophobic end of another lipid or lipid-like molecule. The resulting bilayer membrane is selectively permeable to molecules of a certain size, hydrophobicity, shape, and net charge.

Although most liposomes are lipid or lipid-like in nature, the application of Uster et al., WO 92/03123, published 5 Mar. 1992, describes alternative liposome bilayer formulations, comprising a surfactant with either a lipid or a cholesterol.

Liposomes find many therapeutic, diagnostic, industrial and commercial applications. They are used to deliver molecules which are not easily soluble in water, or when a direct timed release is desired. Because of their selective permeability to many chemical compounds, liposomes are useful as delivery vehicles for drugs and biological materials. The compound(s) that are to be delivered can be provided within the liposomes where they remain protected from the outside environment. Alternatively, the compounds that are targeted for delivery can be incorporated into the lipid bilayer of the liposomes if they are lipophilic or have been chemically linked to the lipids. Upon reaching the target site, the liposomes may be degraded (for example, by enzymes in the gastro-intestinal tract) or they may fuse with the membranes of cells. Degradation of the liposomes or fusion of the liposomes with cell membranes results in releasing the compound.

Several methods of preparing liposomes are known. For a general review of commonly used methods, see Szoka et al., *Ann. Rev. Biophys. Bioeng.*, 9:467–508 (1980). Among the more common of these are 1) sonication of a solution containing lipids sometimes followed by evaporation/lyophilization and rehydration (see, e.g. Stryer, *Biochemistry*, pp. 290–291 (Freeman & Co., New York, 1988), and Ohsawa et al., *Chem. Pharm. Bull.*, 32:2442 (1984)), 2) homogenization of lipid solution, sometimes at high pressure or high shearing force (see e.g. U.S. Pat. No. 4,743,449 issued 10 May 1988, and U.S. Pat. No. 4,753,788 issued 28 Jun. 1988), 3) hydration and sometimes sonication of a dried film of vesicle-forming lipids wherein the lipid film is prepared by evaporation of a solution of lipids dissolved in an organic solvent (see e.g. U.S. Pat. No. 4,452,747 issued 5 Jun. 1984, U.S. Pat. No. 4,895,719 issued 23 Jan. 1990, and U.S. Pat. No. 4,946,787 issued 7 Aug. 1990), 4) lyophilization or evaporation and rehydration (see e.g. U.S. Pat. No. 4,897,355 issued 30 Jan. 1990, EP 267,050 published 5 Nov. 1988, U.S. Pat. No. 4,776,991 issued 11 Oct. 1988, EP 172,007 published 19 Feb. 1986, and Australian patent application AU-A-48713/85 published 24 Apr. 1986), 5) solvent injection or infusion of a lipid solution into an aqueous medium or vice versa (see e.g. Batzri et al., *Biochim. Biophys. Acta*, 298:1015–1019 (1973), U.S. Pat. No. 4,921,757 issued 1 May 1990, U.S. Pat. No. 4,781,871 issued 1 Nov. 1988, WO 87/02396 published 24 Mar. 1988, and U.S. Pat. No. 4,895,452 issued 23 Jan. 1990), 6) spray drying (see e.g. Australian patent application AU-A-48713/85 published 24 Apr. 1986, and U.S. Pat. No. 4,830,858 issued 16 May 1989), 7) filtration (see e.g. WO 85/01161), 8) reverse-phase evaporation (see e.g. Szoka et al., *Proc. Natl. Acad. Sci. USA*, 75:4191–4199 (1978)), and combinations of the above methods (see e.g. Pick *Arch. Biochem. Biophys.*, 212:186–194 (1981), and Kasahara et al., *J. Biol. Chem.*, 251:7384–7390 (1977)).

Methods are also known for atomizing a solution of lipids to form liposomes, however these methods typically require atomization under pressure, which is inefficient and results in a loss of liposome-component solution. U.S. Pat. No. 4,508,703 issued 2 Apr. 1985 discloses preparation of liposomes by dissolving lipids in an appropriate solvent, and atomizing this solution by spraying it through a spray nozzle or atomizer into an enclosed chamber containing a gas heated to a higher temperature than the boiling point of the solvent. The solvent evaporates, and lipid particles and liposomes are formed and collected as a dried mixture. The dried liposomes and lipid particles can then be hydrated in an aqueous medium.

PCT Application WO 89/11850, published 14 Dec. 1989, teaches a method for forming liposomes having an additional material entrapped in the lipid bilayer, or in association with a component of the bilayer, rather than having being entrapped inside the space created by a spherical bilayer. This application teaches that aerosolization may be used, by putting material into a sprayer or trigger pump such as would be commonly used for applying non-pressurized hair sprays, insecticides, and the like to other surfaces. According to this application, upon spraying the formed solution (of lipid and material), it is mixed with air and the volatile solvent evaporates as the solution leaves the nozzle.

U.K. patent application GB 2,145,107A published 20 Mar. 1985 teaches producing an aerosol spray containing liposomes. The liposomes are produced by combining under pressure an aqueous solution and a lipid mixture, and passing the mixture, still under pressure, through a nozzle or other arrangement to produce an aerosol spray containing liposomes.

WO 87/07502 published 17 Dec. 1987 discloses formation of pro-liposome aerosols by spraying under pressure a solution containing one or more volatile liquid propellants, one or more membrane lipids dissolved in the propellant, and one or more biologically active compounds.

EP 357,773 published 14 Mar. 1990 discloses a method of preparing liposomes by dissolving lipids in an organic solvent, evaporating the solvent, adding an aqueous solution to the dried lipid film, ultrasonicating the solution to prepare a homogenous suspension of lipids, injecting the solution with an inert gas to pressurize the solution, and delivering the pressurized solution through a nozzle to form liposomes.

EP 190,926 published 13 Aug. 1986 teaches formation of lipids by first mixing the lipids with an organic solvent, adding water, and then pressurizing this solution and passing it through a nozzle to produce an aerosol spray.

U.S. Pat. No. 5,192,528 teach a method for delivering a therapeutic dosage of a drug to the lungs, for treating a lung condition or disease. An aqueous suspension of liposomes containing the drip in liposome-entrapped form is aerosolized under conditions which produce aerosol particle sizes favoring particle deposition in a selected region of the respiratory tract. These conditions involve the use of a pneumatic nebulizer, wherein the aqueous liposome suspension is placed in the nebulizer, and compressed air is supplied to the nebulizer. The pressurized air forces the liposome suspension through a nozzle having a defined size orifice. This aerosol is then directed against a baffle which traps larger aerosol particles and passes smaller ones. This patent also suggests using an unspecified device suitable for aerosolizing an aqueous suspension of liposomes using ultrasonic energy to break up a carrier fluid into a fine mist of aqueous particles.

EP 335,133 (published 4 Oct. 1989) discloses the incorporation of drugs to be delivered to a patient into a phopholipid/peptide mixture, with the phospholipid/peptide mixture comprising lung surfactant protein and associated lipids. Surfactants are compounds that affect the surface tension of an air-water interface. As such, surfactants can alter the rate of transport of gases across a fluid surface such as a biological membrane in the lung. One important class of surfactants is lung (pulmonary) suffactant which is present on the alveoli and serves to enhance the transport of oxygen across the cell membrane and into these cells.

Lung suffactant is a complex of various lipids and at least three different proteins called SP-A, SP-B, and SP-C. The literature contains various lung suffactant protein preparations, including those with DPPC. Generally, preparations can be classified into five types. These include 1) natural human surfactant (purified from human amniotic fluid), (Merritt, et al., N. Engl. J. Med. 315:787, 1986), 2) semisynthetic surfactant (prepared by combining DPPC and high density lipoprotein), (Halliday, et al, Lancet 1:476, 1984), 3) animal lung surfactant (isolated by organic extraction of the whole lung or lavage fluid), (Fujiwara, supra; Enhorning, et al., Pediatrics 76:145, 1985; Kwong, et al., Pediatrics 76:585, 1985), and 4) purified human surfactant apoproteins (SP-A, SP-B, and/or SP-C purified from natural sources or derived by recombinant DNA technology; see Jobe et al., Am. Rev. Resp. Dis. 136:1032, 1987, and Glasser et at., J. Biol. Chem. 263:10326, 1988) which are reconstituted with surfactant lipids (Revak, et al. J. Clin. Invest. 81:826, 1987).

Ultrasonic atomizing nozzles are commercially available, which atomize liquids without the use of pressure, such as those made by the SONO-TEK Corporation, Poughkeepsie, N.Y., including their Series 8700-120 nozzle. This SONO-TEK nozzle is suggested by the manufacture as suitable for coating medical products with proteins, antibodies, silicones, lubricants, diagnostic and disinfectant materials, and for drug encapsulation. See also, e.g., U.S. Pat. No. 4,301,968 issued 24 Nov. 1981 which discloses an ultrasonic atomizer that uniformly atomizes a solution and that is capable of varying the flow rate of the solution through the atomizer. U.S. Pat. No. 4,337,896 issued 6 Jul. 1982 discloses an ultrasonic fuel atomizer with an atomizing surface capable of producing a cone-shaped spray pattern with a predetermined cone angle and a uniform dispersion pattern of the solution.

While many of the above cited references disclose methods of preparing liposomes, the methods are multi-step and thus cumbersome and labor intensive, or result in wasting lipid and/or other bilayer-forming material, or have a low rate of incorporation of the active agent or passenger molecule desired to be incorporated into or associated with the liposome.

Accordingly, it is an object of the present invention to provide an economic and efficient method of preparing liposomes suitable for use on a large scale. This and other objects will be apparent to one of ordinary skill in the art.

SUMMARY OF THE INVENTION

In accordance with the objects of this invention, methods are provided for preparing liposomes comprising preparing a first solution of bilayer-forming materials (such as lipids, surfactants, or lipid-like bilayer-forming materials), and any optional passenger molecule, and without added pressurization spraying the first solution onto or below the surface of a second solution, thereby forming a liposome suspension. Without being limited to any particular mechanism of action, it is believed that, as the solvent is extracted and diluted in the second solution, the bilayer-forming materials (and to some extent the passenger molecules) become insoluble, forming liposomes instantly.

Following the liposome formation, the suspension may be concentrated, such as by ultrafiltration. A preferred embodiment of this invention uses a tangential flow stack comprised of a Filtron membrane module. After the desired liposome concentration is reached, residual solvent may be removed, such as by diafiltration with fresh buffer if desired.

The concentrated liposome suspension may be further processed, such as by formulating the suspension for use, or introducing the liposomes into vials or other containers and lyophilized or otherwise readied for storage. For extended storage, it is currently preferred that the product be lyophilized and kept below the temperature at which the frozen molecules are immobile and below any phase transitions.

In one preferred embodiment, the first solution is comprised of lipids dissolved in an organic solvent such as isopropyl alcohol, and the second solution is aqueous.

In another preferred embodiment, the bilayer-forming materials of the first solution include lipids and/or proteins present in naturally occurring lung surfactants, and the liposomes that are produced have a therapeutic use for patients having or at risk of having respiratory distress.

In the methods of this invention the first solution is sprayed through a nozzle that vibrates at ultrasonic frequencies, using a method which does not require pressurizing the first solution above atmospheric pressure during the spraying of this solution.

BRIEF DESCRIPTION OF THE DRAWINGS

FIG. 1 illustrates a schematic example of the novel process of this invention.

DETAILED DESCRIPTION OF THE INVENTION

This invention describes new and useful methods for the preparation of liposomes for use in the delivery of therapeutic, diagnostic or cosmetic agents. The present invention provides an economic and efficient method of preparing liposomes on a large scale.

I. Preparing Liposome Compositions

A. Liposome Components are typically amphipathic materials which can form a closed lamellar bilayer phase (referred to herein as "bilayer forming materials"), plus additional materials to be delivered or useful in targeting delivery or conferring useful properties on the liposome such as extended half-life, and solvent. Mixtures of components may be used.

1. Lipids and lipid-like components suitable for use in this invention include phospholipid, a mixture of phospholipid, polar lipids, neutral lipids, fatty acids, and their derivatives. A preferred lipid has the characteristic that when dispersed alone in water, at a temperature above the lipid transition temperature, they are in a lipid emulsion phase. In certain embodiments, the lipid is a single-aliphatic chain lipid of greater than about 12 carbons and can be either saturated or unsaturated, or substituted in other ways. Suitable lipids include the ester, alcohol, and acid forms of the following fatty acids: stearate, oleic acid, linoleic acid, arachidate, arachidonic acid, and other single-aliphatic chains acids. Further candidates include the ester, alcohol, and acid forms of the retinols, in particular, retinol and retinoic acid.

Particularly preferred lipids include phosphatidylcholine (PC), phosphatidylglycerol (PG) and their derivatives, synthetically created or derived from a variety of natural sources.

In certain embodiments, the liposome is sterically stabilized by the incorporation of polyethylene glycol (PEG), or by the PEG headgroups of a synthetic phospholipid (PEG conjugated to distearoyl phosphatidylethanolamine (DSPE), see e.g. the method of Papahadjopoulos et al., *Proc. Natl. Acad. Sci. USA* 88:11460–11464 (1991), hereby incorporated by reference.

2. Surfactants are suitable bilayer forming materials for use in this invention, typically a surfactant with good miscibility such as Tween, Triton, sodium dodecyl sulfate (SDS), sodium laurel sulfate, or sodium octyl glycoside. A preferred surfactant forms micelles when added to aqueous solution above the suffactant's phase transition temperature and is composed of one or more aliphatic chains. These aliphatic chains may be saturated, unsaturated, or substituted in other ways, such as by ethoxylation; typically the aliphatic chain contains greater than about 12 carbons. Additional suitable surfactants include the following: lauryl-, myristyl-, linoleyl-, or stearyl- sulfobetaine; lauryl-, myristyl-, linoleyl- or stearyl-sarcosine; linoleyl, myristyl-, or cetyl- betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT series (Mona Industries, Inc., Paterson, N.J.).

The application of Uster et al, WO 92/03123, published 5 Mar. 1992, describes alternative liposome bilayer formulations, comprising a surfactant with either a lipid or a cholesterol. These ingredients and the methods for their use are specifically incorporated by reference.

3. Sterols and sterol esters are also suitable for use in this invention, including cholesterol, cholestanol, cholesterol sulfate and other cholesterol analogs and derivatives.

4. Double chain glycerophospholipids may also be incorporated into the liposomes of this invention.

5. Additional agents are desirably incorporated into or associated with the liposomes of this invention. These additional agents are referred to herein as "passenger molecules", and are materials intended to solubilize in the liposome and be retained in the space formed within the spherical bilayer, or to be retained within a formed bilayer or associated with that bilayer. Incorporation of passenger molecules is readily accomplished by mixing a solution of the passenger molecule with a preformed liposomal suspension and incubating until the insertion of the passenger molecules into the liposomal bilayer. Alternatively, the passenger molecules are admixed with the bilayer-forming materials used in the preparation of the liposomes. Alternatively, the passenger molecules and the liposomes are formulated into conventional pharmacologically acceptable vehicles as described below.

Passenger molecules such as antimicrobials, antivirals (e.g. fluorouracil, iodouridine, trifluorouridine, vidarabine, azidothymidine, ribavirin, phosphonofomate, phosphonoacetate, and acyclovir) anti-inflammatory agents (e.g. prednisolone, dexamethasone, and non-steroidal anti-inflammatories) anti-cancer drugs (such as cis-platin or 5-fluorouracil), anti-parasitics, anti-allergic and anti-asthmatic agents (such as allergens, cromolyn, cemetidine, naphazoline, lodoxamide, ephedrine and phenylephinephrine), dyes, fluorescent compounds, radiolabels (e.g. as iodine, rhenium, tritium, alpha particle-emitting isotopes), radio-opaque compounds, vitamins, minerals, plasmids, vectors, viral particles, peptides, proteins, glycoproteins, lipoproteins, nucleotides, carbohydrates (such as natural or synthetic mono and polysaccharides and sugars), receptors, growth factors, hormones, neurotransmitters, tumorocidal agents, growth factors, toxins, analgesics, anesthetics, narcotics, catalysts, enzymes, and other biologically active inorganic and organic molecules are examples of the classes of substance which may be utilized. It is most preferred that the passenger molecule be lipophilic, however hydrophilic material may also be utilized if they are capable of forming an association with the bilayer (i.e., with a polar head group). While this list is extensive it is by no means intended to be exclusive, merely exemplary.

The term "cytotoxic moiety" as used herein is intended to include isotopes as cytotoxic radiopharmaceuticals and toxins, such as a cytotoxic drugs or an enzymatically active toxin of bacterial, fungal, plant or animal origin, or an enzymatically active fragment of such a toxin. Enzymatically active toxins and fragments thereof used are diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes.

The invention encompasses cytotoxic moieties encompassed within the liposome, or conjugated to the liposome. Conjugates of the liposome and such cytotoxic moieties are made using a variety of bifunctional protein coupling agents. Examples of such reagents are SPDP, IT, bifunctional derivatives of imidoesters such as dimethyl adipimidate Hcl, active esters such as disuccinimidyl suberate, aldehydes such as glutaraldehyde, bis-azido compounds such as bis(p-azidobenzoyl)hexanediamine, bis-diazonium derivatives such as bis-(p-diazoniumbenzoyl)-ethylenediamine, diisocyanates such as tolylene 2,6-diisocyanate and bis-active fluorine compounds such as 1,5-difluoro-2,4-dinitrobenzene. The lysing portion of a toxin may be joined to the liposome. A particularly preferred toxin is the ricin A chain. Most advantageously the ricin A chain is deglycosylated or produced without oligosaccharides, to decrease its clearance by irrelevant clearance mechanisms (e.g., the liver) and produced through recombinant means. In another embodiment, whole ricin (A chain plus B chain) is conjugated to the liposome or incorporated into the liposome if the galactose binding property of B-chain can be blocked ("blocked ricin"). An advantageous method of making a ricin immunotoxin suitable for use as a passenger molecule or attached to a liposome is described in Vitetta et al., *Science* 238:1098 (1987) hereby incorporated by reference.

In a further embodiment toxin-conjugates are made with Fab or $F(ab')_2$ fragments. Because of their relatively small size these fragments can better penetrate tissue to reach infected cells. These conjugates may be used as a passenger molecule or attached to a liposome.

In another embodiment, fusogenic liposomes are filled with a cytotoxic drug and the liposomes are coated with antibodies specifically binding an infected cell, such as a T-cell presenting on its surface a HIV antigen The term "biologically active molecule" is defined herein as a naturally occurring or synthetic compound which has an effect on an organism to which it is administered. Representative examples of biologically useful polypeptides include, among others, nucleoproteins, glycoproteins, and lipoproteins. Liposomes made according to this invention are also used to delivery nucleic acids for gene therapy, to provide properly functioning replacement genes, or to introduce a new or enhanced gene functionality. Many protein classes are suitable for use in this process, including antibodies, enzymes, hormonally active polypeptides, immune modulators such as lymphokines, monokines and cytokines, growth regulatory and stimulatory proteins, blood proteins, and antigens for viral, bacterial and parasitic vaccines. Specific examples of suitable proteins include alpha-, beta- and gamma-interferon, tumor necrosis factor-alpha and tumor necrosis factor-beta, plasminogen activators such as tissue plasminogen activator or urokinase or streptokinase, relaxin, immunoglobulins, CD4, TGF-$\alpha$ and TGF-$\beta$, DNase, VEGF, NGF, NF, activin, inhibin, EGF, IGF, enkephalinase, blood clotting factors including factor VIII and tissue factor as well as fragments or amino acid sequence variants thereof and antibodies thereto. Examples of other biologically active molecules that can be used in this process include steroids, lipids, synthetic and naturally occurring drugs, tumoricidal agents (such as doxorubicin) nucleic acids, and amino acids.

In one preferred embodiment, the biologically active molecule comprises a component of natural pulmonary surfactant, such as DPPC, POPG, or one or more of the proteins known as the SP-A, SP-B, and/or SP-C proteins of lung surfactant. The surfactants may be part of the bilayer, and alternatively or additionally may be presented within a liposome. Lung surfactant may be prepared by known methods from synthetic dipalmitoylphosphatidylcholine (DPPC), egg or synthetic phosphatidylglycerol (PC), and purified surfactant apoproteins (SP-B and/or SP-C and/or SP-A). Purified surfactant apoproteins are obtained by recombinant methods or direct synthesis using published nucleotide and amino acid sequences (Glasser, et al., Proc. Natl. Acad. Sci. U.S.A. 84:4007, 1987; Jacobs, et al., J. Biol. Chem. 262:9808, 1987; Floros, et al., J. Biol. Chem. 261:9029, 1986; White, et al., Nature 317:361, 1985; Whitsett, et al., Pediatr. Res. 19:501, 1985; Warr, et al., Proc. Natl. Acad. Sci. U.S.A. 84:7915, 1987; Hawgood, et al., Proc. Natl. Acad. Sci. U.S.A. 84:66, 1987; Glasser, et al., J. Biol. Chem. 263:9, 1988, Glasser, et al., supra J. Biol. Chem. 263: 10326, 1988; and Jobe et al., Am. Rev. Resp. Dis. 136: 1032, 1987). Desirably, surfactant apoproteins are reconstituted with surfactant lipids, Revak, supra.

Cosmetics or cosmetic ingredients such as hair sprays, colorants, dyes, and the like are appropriate for incorporation into a liposome. Medicaments used in mouthwashes, throat sprays, antiseptic sprays and the like are also suitable for use in the practice of this invention.

Drugs or other agents for therapeutic or diagnostic administration may be incorporated into or associated with a liposome according to the present methods, and specifically targeted to a site within a patient. In preferred embodiments, therapeutic and diagnostic agents are effectively administered to a patient by coupling a liposome comprising or associated with those agents to a monoclonal antibody or immunoglobulin fragment (such as a Fab' fragment), a receptor, adhesion molecule, ligand or other targeting moiety.

In yet other embodiments, the liposome incorporates or is associated with a glycophospholipid-linked polypeptide. In one example of this embodiment, the carboxyl terminal domain that specifies glycophospholipid membrane anchor attachment for mDAF (Decay Acceleration Factor), referred to as the GPI signal domain, (wherein GPI is an abbreviation of glycophosphatidylinositol), or functionally equivalent domains from other proteins which also are anchored by glycophospholipids, are fused to proteins or multimers of such proteins which are heterologous to the source of the GPI signal domain, for example hormones, antigens (especially infectious organisms), allergens, immunoglobulins, enzymes, receptors and the like, including gp120, CD4, a plasminogen activator. See e.g. U.S. Ser. No. 08/017,934, filed 12 Feb. 1993.

Combinations of passenger molecules are desirable. For example, in a particularly preferred embodiment, liposomes within which a toxic drug has been packaged, and further comprising or associated with GPI-linked to CD4, are thus targeted to HIV-infected cells which express gp120 on their surfaces. Similar GPI fusions to ligands or antibodies can be used to target liposomes containing toxic agents to cancer cells having receptors or antigens which specifically bind to the ligands or antibodies.

Combinations of antibody-like targeting domains with radioisotopes or toxins are encompassed within this invention, as are other combinations of targeting moieties and biologically active molecules, and combinations of therapeutic passenger molecules.

6. Solvents are utilized for solubilizing the bilayer-forming material and any passenger molecules. The appropriate solvent is selected from those able to solubilize both the amphipathic material(s) and the passenger molecule. Generally, the most preferable solvent is a low molecular weight hydrocarbon such as ethanol, propanol, butanol, isopropanol, chloroform, acetone, methylene chloride or propyl glycol and the like. In addition, the solvent must be appropriate for the particular use intended for the liposome. If the liposome is to be employed in vivo, the solvent must be utilizable without causing toxicity in that application and generally must be pharmaceutically acceptable and readily miscible. In other applications, such as in a commercial process or for a pesticide, the toxicity of the solvent is not as critical, but its volatility is also a selection factor. Methylene chloride is an example of a solvent which is useful in many processes. Mixtures of solvents may be appropriate in some circumstances.

In preferred embodiments, an alcohol, and more preferably a short chain alcohol such as isopropyl alcohol, serves as a suitable solvent.

B. Liposome Preparation according to this invention involves a spray technique to form liposomes directly by spraying a first solution of solvent and bilayer-forming material (and any passenger molecules) onto the surface of a second solution, often a buffer. Without being limited to any particular mechanism of action, it is believed that, as the solvent is extracted and diluted in the buffer, the bilayer-forming materials (and to some extent the passenger molecules) become insoluble, forming liposomes instantly.

The solubility of bilayer-forming materials and any passenger molecules in a solvent, such as an organic solvent, will vary depending on the components used, and may also vary with temperature. Certain lipids, for example dipalmitoyl-phosphatidylcholine (DPPC) are quite insoluble at room temperature and below; in these circumstances the first solution may be held at a temperature above room temperature, such as between about 45°–75° C., during the spray process. Optimization of the solubility of the components used in this process will be determined by routine experimentation. It is further presently believed that spraying above or below the melting point of a lipid component may affect whether a passenger molecule is encapsulated within a lipid bilayer or is integrated into the lipid in another fashion, and the determination of the proper temperature conditions for any particular application of this invention will be routine.

To prevent oxidation of the lipids, the solution comprising the liposome components may be kept under a constant stream of an inert gas such as nitrogen to produce a dry nitrogen atmosphere.

In a preferred embodiment of this invention, the first solution comprises DPPC, palmitic acid, palmitoyl-oleoyl-phosphatidylglycerol (POPG), Lung Surfactant Protein C (SP-C), in isopropyl alcohol (IPA). This first solution is sprayed onto a second, buffer solution comprising succinic acid, disodium succinate hexahydrate, and purified water at approximately pH 6.5. In this embodiment the first solution is heated to about 55°–65° C. for mixing and spraying.

The bilayer-forming material and passenger molecules may be prepared in separate solutions and then combined, optionally with stirring.

The spray process equipment is assembled in a fashion similar to that shown in FIG. 1, although different configuration of the indicated components, or different equivalent components, may be used.

The first solution is introduced into a reservoir. A filter may be provided on the outlet of this reservoir, and connecting means are provided between the reservoir and a nozzle provided in the spray chamber.

The second solution is introduced into the spray chamber, in some preferred embodiments at a level which does not directly contact the spray nozzle. In certain embodiments, the second solution circulates between the spray chamber and a mixing chamber, such as by peristaltic pumps at about a liter/min. The solution in the spray chamber (and any mixing chamber) is preferably stirred, in some embodiments at about 200 rpm, and may be heated to a temperature similar to that of the first solution.

In alternate embodiments, the nozzle is immersed in the second solution, and the organic or other first solution solvent is removed, such as by ultrafiltration and/or diafiltration, or by being pulled out the top of the spray chamber by a vacuum. This alternate method is advantageous where the first solution solvent is immiscible in water to facilitate size consistency among the liposomes formed.

When all solutions and equipment are ready, the nozzle is provided with necessary power supply, The level of first solution and or inert gas in the reservoir is adjusted to begin flow of the first solution to the nozzle. This flow is regulated to obtain a uniform spray pattern from the nozzle. This flow is continued until the desired amount of first solution has been sprayed (typically the entire amount).

A variety of commercially available nozzles or similar devices exist that can be used for atomizing a bilayer-forming solution to form liposomes. According to this invention, nozzles which do not require high pressure to operate are suitable. Preferred embodiments utilize a spray nozzle which uses an ultrasonic high frequency to form a mist spray, generally ultra-fine and with low velocity. Such preferred nozzles reduce solution wasting because the need to prime the nozzle is reduced or eliminated. Suitable ultrasonic atomizing nozzles are made by the SONO-TEK Corporation, Poughkeepsie, N.Y., such as their Series 8700-120 nozzle. Atomization occurs as liquid comes into contact with the vibrating nozzle tip. Tiny drops are formed when the ultrasonic energy exceeds the liquid's surface tension. Drop size distribution is determined by the nozzle frequency, surface tension, and the density of the liquid being atomized, with frequency being the key factor in defining the range of drop diameters for a given size nozzle.

The nozzle atomizing frequency, nozzle bore, and other nozzle characteristics are selected to produce the appropriate flow and desired size particles. Without intending to be limited to a particular theory of mechanism, generally, the frequency at which the nozzle operates tends to establish the size of the atomized particle and relates to the size of liposomes formed; the higher the frequency, typically the smaller the drops in the spray, and hence generally the smaller the liposome eventually formed. A high frequency nozzle typically requires a relatively small nozzle size, resulting in a low flow capacity and smaller spray particles. A low frequency nozzle typically requires a large nozzle size, resulting in a higher flow capacity and larger spray particles. In addition to the nozzle characteristics, the temperatures and formulations of the first and second solutions (including the solvents used and the characteristics of any passenger molecules) also have an influence on the liposome sizes recovered from the nozzle spray.

Nozzle flow capacity is an important consideration in the practice of this invention. In one preferred embodiment, the SONO-TEK Series 8700-120 nozzle is used, with a nozzle flow capacity of 0/5 gph (0.5 ml/s) for 0.052 diameter bore. A system incorporating this nozzle was able to process about 0.2 liters per hour of first solution. In other preferred embodiments, nozzles are utilized which operate at a lower frequency and has more than 5 times the capacity, preferably 7 times the capacity (1.4 liters/hour). In certain other embodiments, more than one nozzle is used.

The resulting mixture of first solution and second solution may be collected in a main mixing tank. Further processing may be commenced immediately, or the tank may be stored, or the solutions drained into another container (provided sterile in certain pharmaceutical-related applications) for storage. Storage may be at room temperature or reduced. For pharmaceutical-related products, storage at about 5° C. and for about one week or less is recommended before further processing.

C. Liposome Recovery is commenced at a time following the liposome formation, the suspension. The liposome suspension may be used without further processing for certain applications. For other applications, it is desired to recover the liposomes from the second solution. The may be accomplished by a variety of known methods, such as filtration or chromatographic separation of the liposomes.

In preferred embodiment, the liposomes are concentrated using ultrafiltration, for example using a tangential flow stack comprised of a Filtron 100 KD membrane module.

After the desired liposome concentration is reached, the residual solvent may be flushed out by diafiltration with fresh buffer if desired.

In particularly preferred embodiments, the filter membrane system with pumps and connection lines as necessary, are flushed with water and steamed in place (or autoclaved) for sterility. The system is next flushed with extra second solution or other buffer as desired for a short period of time, approximately 0–30 minutes, and preferably 10–15. The liposome suspension is circulated through the filter system, generally at rate a preferred rate of about 1–5 (and preferably 2) liters/min, and continued for about 5 minutes. Next the flow is restricted at the concentrate line until the system is pressurized to approximately 8 psi transmembrane pressure. This process is continued until the desired final concentrate volume is reached. In preferred embodiments, the concentrate is also diafiltered with six volumes of fresh second solution. The filtration system is advantageously drained by pressuring with air. The concentrated liposome suspension is collected. If desired, the final suspension volume is measured and may be diluted or further concentrated if desired for a particular application.

D. Liposome Sizing. Without being limited to a particular theory of operation, it is believed that the clearance rate of liposomes from blood or tissue depends on their particle size as well as the specific ingredients they contain. In certain embodiments, liposomes are selected for therapeutic administration which are approximately 50–100 nm in diameter, or larger. In other embodiments, faster clearance is desired or smaller size is advantageous for other reasons, and liposomes are selected of less than 50-nm diameter. The size of the liposome may also be related to its stability; in some embodiments for example, a larger size liposome can be relatively unstable, compared to a smaller liposome, and the selection criteria may take advantage of this feature. For example, a relatively large sized and relatively unstable liposome may be useful for administration of pharmaceuticals in the lung, where instability leads to rapid spreading of components. The size of the liposome for any particular application, whether therapeutic, diagnostic, commercial, industrial, or cosmetic, shall be selected according to the characteristics desired.

The liposome suspension may be sized to achieve a selective size distribution having optimal properties. Several techniques are available for reducing the sizes and size heterogeneity of liposomes. Sonicating a liposome suspension either by bath or probe sonication produces a progressive size reduction down to less than about 0.05 microns in size. In a typical homogenization procedure, liposomes are recirculated through a standard emulsion homogenizer until selected liposome sizes are observed. In both methods, the particle size distribution can be monitored by conventional laser-beam particle size discrimination.

Extrusion of liposomes through a small-pore polycarbonate membrane is an effective method for reducing liposome sizes down to a relatively well-defined size distribution, depending on the pore size of the membrane. Typically, the suspension is cycled through the membrane several times until the desired liposome size distribution is achieved. One such filter is the 0.45 µm Acrodisc filter (Gelmar Sciences, Inc., Ann Arbor, Mich.). The liposomes may be extruded through successively smaller-pore membranes, to achieve a gradual reduction in liposome size.

Centrifugation and molecular sieve chromatography are other methods which are available for producing a liposome suspension with particle sizes below a selected threshold of 1 micron or less. These two methods both involve preferential removal of larger liposomes, rather than conversion of large particles to smaller ones; liposome yields are correspondingly reduced.

Particle size may be determined according to known methods, such as by using the Brinkman 2010 which used laser interference, and by the Nicomp 200 which uses laser light scattering. The Brinkman 2010 can resolve particle populations in the 5–100 µm range, while the Nicomp 200 can resolve in the 5–5000 nm range. Alternate methods for covering the range of 100–1000 nm may involve a FACS analyzer.

E. Removing Non-Integrated Passenger Molecules And Bilayer-Forming Material is desirable to increase the ratio of liposomes having an entrapped passenger molecule to free materials. Several methods are available for removing free material from a liposome suspension. Sized liposome suspensions can be pelleted by high-speed centrifugation, leaving free material and very small liposomes in the supernatant. Another method involves concentrating the suspension by ultrafiltration, then resuspending the concentrated liposomes in a replacement medium. Alternatively, gel filtration can be used to separate larger liposome particles from solute molecules. Also, some free material can be removed using ion-exchange or affinity chromatography to bind the free material in its free form, but not in liposome-bound form.

A certain degree of removal of undesired components may be accomplished during the ultrafiltration/diafiltration process described above.

F. Sterility may be an important process consideration for liposomes designed for in vivo or in vitro use. If desired, spray nozzles, filters, tubing, spray chambers, mixing tanks, feed solution reservoirs, and fittings etc. may be autoclaved or other wise sterilized. Mixing tanks or other components may be sanitized, such as by filing with a alcohol solution (e.g. 70 v/v % IPA) and drained, and/or by introduction of steam.

The concentrated liposome suspension may be further processed, such as by formulating the suspension as described infra, or filled into vials or other containers and lyophilized for storage. The product bottles or other containers may be provided sterile. For extended storage, it is currently preferred that the lyophilized product be kept below the temperature at which the frozen molecules are immobile and below any phase transitions.

Lyophilization cycles typically involve a freezing cycle (at about −550° C.) for several hours, followed by one or more drying cycles, according to standard methods.

II. Formulations and Uses

This invention provides novel methods for the preparation of liposomes which can be used in a variety of formulations and for a variety of diagnostic, commercial, cosmetic, industrial, and therapeutic uses.

For therapeutic use, the liposomes are placed into pharmaceutically acceptable, sterile, isotonic formulations together with required cofactors, and optionally are administered by standard means well known in the field. The formulation is preferably liquid, and is ordinarily a physiologic salt solution containing non-phosphate buffer at pH 6.8–7.6, or may be lyophilized powder. Liposomes may be formulated with pharmacologically acceptable detergents such as Tween 20 or polyethylene glycol (PEG), or with serum albumin.

It is envisioned that a therapeutic administration of liposomes may comprise liposomes incorporating passenger molecules plus liposomes free from those passenger molecules, which combination may beneficially alter the distribution or delivery of the passenger molecule.

As an example of an application of the liposomes of this invention to therapeutic liposome administration, patients suffering from disorders characterized by the absence of a critical enzyme activity, as for example in inborn errors of metabolism, are treated by an infusion of a liposome comprising the enzyme in question fused to a phospholipid anchor (GPI) domain. The kinetics of synthesis and delivery to the cells of the required metabolite are improved over simply infusing the metabolite. The liposome is injected into the cerebrospinal fluid, e.g., in order to address metabolic deficiencies of brain cells, or into the lymph system or blood stream as required to optimally target other tissue or organ system-specific disorders.

The liposome compositions to be used in therapy will be formulated and dosages established in a fashion consistent with good medical practice taking into account the disorder to be treated, the condition of the individual patient, the site of delivery of the isolated polypeptide, the method of administration and other factors known to practitioners.

The liposome is prepared for administration by mixing the liposome at the desired degree of purity with physiologically acceptable carriers i.e. carriers which are nontoxic to recipients at the dosages and concentrations employed, or adjuvants. In certain embodiments, an adjuvant is incorporated with a passenger molecule into the liposome. Adjuvants and carriers are substances that in themselves share no immune epitopes with the target antigen, but which stimulate the immune response to the target antigen. Ordinarily, this will entail combining a passenger molecule with buffers, low molecular weight (less that about 10 residues) polypeptides, proteins, amino acids, carbohydrates including glucose or dextrans, chelating agents such as EDTA, and other excipients. Freunds adjuvant (a mineral oil emulsion) commonly has been used for this purpose, as have a variety of toxic microbial substances such as mycobacterial extracts and cytokines such as tumor necrosis factor and interferon gamma (described in co-pending U.S. Ser. No. 07/007,075). Although passenger molecules which are antigens are desirably administered with an adjuvant, either within the liposome or accompanying the liposome in a formulation, in situations where the initial inoculation is delivered with an adjuvant, boosters with antigen may not require adjuvant. Carriers often act as adjuvants, but are generally distinguished from adjuvants in that carriers comprise water insoluble macromolecular particulate structures which aggregate the antigen. Typical carriers include aluminum hydroxide, latex particles, bentonite and liposomes. Saponin derivatives are also preferred adjuvants.

It is envisioned that injections (intramuscular or subcutaneous) will be the primary route for therapeutic administration of the liposomes of this invention, intravenous delivery, or delivery through catheter or other surgical tubing is also used. Alternative routes include tablets and the like, commercially available nebulizers for liquid formulations, and inhalation of lyophilized or aerosolized liposomes. Liquid formulations may be utilized after reconstitution from powder formulations.

The liposomes of this invention may also be administered via other microparticulate delivery systems or sustained release formulations placed in certain tissues including blood. Suitable examples of sustained release carriers include semipermeable polymer matrices in the form of shaped articles, e.g. suppositories, or microcapsules. Implantable or microcapsular sustained release matrices include polylactides (U.S. Pat. Nos. 3,773,919, EP 58,481) copolymers of L-glutamic acid and gamma ethyl-L-glutamate (U. Sidman et al., *Biopolymers* 22(1):547–556, (1985)), poly(2-hydroxyethyl-methacrylate) or ethylene vinyl acetate (R. Langer et al., *J. Biomed. Mater. Res.* 15:167–277 (1981) and R. Langer, *Chem. Tech.* 12:98–105 (1982)). Pharmaceutically acceptable polymers, such as collagen, polylysine, polylactic acid, polymethylacrylate, polyurethane, polyglycolic acid, hydroxypropylcellulose, agar and agarose, are also suitable carriers for liposomes of this invention. Methods for preparing these polymers in cross-linked and/or gel form are well known, and the methods can be readily adapted to incorporate liposomes. Many of the polymers, such as agar, collagen, and polyurethanes can be formulated in permeable cross-linked structures which allow liposome movement through and out of the matrices at a selected rate. Matrices of this type are suitable for drug delivery in body cavities, where the matrix can be held in place over an extended period, or for ocular use, where an implant can take the form of a clear lens. Other polymer compositions, like polylactate, can be formulated as a biodegradable solid which releases the entrapped liposome slowly over an extended polymer degradation period. Such matrices are suitable for liposome release in the mouth or stomach. Some of the polymer compositions, such as polylysine, can be polymerized in a liposome suspension to form a polymer shell about individual liposomes, to form a coating which, for example, would protect the liposomes from rapid breakdown in the stomach.

In certain embodiments of this invention, the liposomes are of the small (about 200–800 Angstroms) unilamelar type in which the lipid content is greater than about 30 mol. % cholesterol, the selected proportion being adjusted for the optimal rate of the leakage of the passenger molecules.

The dose of the liposome or passenger molecule administered will be dependent upon the properties of the liposome and passenger molecule employed, e.g. its binding activity and in vivo plasma half-life, the concentration of the liposome and passenger molecule in the formulation, the administration route, the site and rate of dosage, the clinical tolerance of the patient involved, the pathological condition afflicting the patient and the like, as is well within the skill of the physician. Generally, doses of from about $0.5 \times 10^{-8}$ to $5 \times 10^{-9}$ molar of passenger molecule per patient per administration are preferred, although the dosage will certainly depend on the nature of the passenger molecule. Different dosages may be utilized during a series of sequential administrations.

For use in vitro for diagnostic purposes, the liposomes will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques.

Liposome compositions, when applied topically, can provide controlled release of a variety of topical medications, such as anti-bacterial or anti-fungal agents, and steroids, and can also serve as a source of moisturizing lipids.

Paste or foam formulations of the liposomes provide advantages of relatively good storage stability and high drug capacity. Liposome pastes or foams are suitable for application to burned or broken skin, ocular tissue, and in body cavities, where the high viscosity of the material helps maintain the material at the site of the application. The concentrate for paste or foam formulations is preferably formed by ultrafiltration with continued recycling of the liposome suspension material. Liposome paste formulations according to this invention are suitable for topical use without additional processing.

Liposome foams can be prepared using conventional two-chamber propellant devices, such as are used for cosmetic foams, such as shaving cream or hair-styling mousse. A heavy liposome suspension contained in one chamber is mixed with propellant gas contained in a second chamber, and the gassified mixture or foam is expelled under the propellant release pressure through a discharge nozzle. U.S. Pat. No. 3,326,416 describes a two-chamber propellant foam device which could be readily adapted for use in liposome foam generation.

Depending to some extent upon the hydrophilic moieties of the bilayer forming materials present in a liposome, the liposome may have a net anionic or cationic charge, or it may be charge neutral. For example, liposomes formed with lipids containing phosphate or sulfate groups will typically be anionic, lipids containing amino groups will be typically cationic, and lipids with polyethyleneoxy groups or glycols typically will have no net charge.

Under conditions of low ionic strength, charged liposomes in an aqueous suspension repel each other and, as a result, the liposomes become ordered in the solution giving a viscous consistency to the liposome suspension, i.e. a gel-like consistency. This is the situation with the liposomes of the present invention which are formulated with anionic surfactants. An increase in the viscosity of charged liposome suspensions can be obtained by ultrafiltration.

Aerosolized liposomes, or liposome sprays are a convenient vehicle for applying the liposomes to nasal or oral mucosa, or for delivery into the respiratory tract. In one embodiment, the liposomes are formulated as a dilute aqueous suspension and sprayed from a conventional pump or squeeze spray bottle. Alternatively, the liposomes are formulated for use with fluorocarbon propellant solvents in a pressurized canister system. Liposomes are also desirably used with nebulizing equipment. Aerosol delivery of liposomes is particularly suited for delivery of lipids and passenger molecules to the lungs, for treating a lung condition or disease. For example, lung surfactant lipids and lung surfactant-associated proteins are desirably delivered via aerosolized liposome to an infant or other individual having or at risk of having respiratory distress. The liposomes may be aerosolized under conditions which produce aerosol particle sizes favoring particle deposition in a selected region of the respiratory tract, see e.g. Radhakrishnan, U.S. Pat. No. 5,192,528.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention. All literature citations herein are expressly incorporated by reference.

EXAMPLES

Lung Surfactant Process Outline

A process was developed for producing liposomes comprising lung surfactant lipids and a lung surfactant protein (SP-C).

I. Liposome preparation
  A. Preparation of succinate buffer (second solution):
   1. The amount of buffer to be prepared was based upon the mount of SP-C to be processed. To determine the volume (in mL) of recirculating succinate buffer required in initial liposome formation, the weight (in mg) of SP-C to be included in the first solution (SP-C bulk) was multiplied by 20. The volume of buffer required for diafiltration was estimated to be six times the volume of final liposome concentrate to be washed. To obtain 0.02M succinate buffer at pH=6.5, we dissolved 0.00064 moles of succinic acid and 0.01936 moles of disodium succinate per liter solution.
   2. The buffer recirculation tank was charged with the required amount of buffer and gently heated with stirring to 65° C.
  B. Dilution of SP-C bulk solution:
   1. Prior to mixing with lipids, the SP-C bulk solution was adjusted to a concentration of 0.45 mg SP-C per mL. The dilution was done with an IPA/H$_2$O (isopropyl alcohol and water) solution of identical composition with the original bulk.
   2. The dilute SP-C solution was allowed to warm to room temperature before adding it to the lipids.
  C. Preparation of lipid solution:
   1. Lipids were weighed out according to the following weight ratio formula; 14 DPPC:6 POPG:2PA:1 SP-C. All weighings were done under a dry inert atmosphere to minimize the potential for water absorption and oxidation.
   2. Lipids were then dissolved in enough warmed reagent grade IPA to give a final solution that was 23.3 mg/mL DPPC, 10.0 mg/mL POPG, and 3.3 mg/mL PA. The dissolution of lipids was accomplished at temperatures $\geq 48°$ C. and were performed under an atmosphere of N$_2$. The inconsistent amount of palmitic acid (PA) used in these steps was not necessarily recommended.
  D. SP-C lipid spray solution:
   1. The room temperature SP-C solution was slowly added to the warmed stirring lipid solution. Care was taken to add the protein slowly in order to avoid precipitating the lipids.
   2. The SP-C lipid mixture was gently heated to 65° C. while maintaining both stirring and N$_2$ blanketing.
  E. Liposome formation/spraying procedure:
   1. Once both recirculating buffer and SP-C lipid solution reached 65° C., the spraying procedure began. The first step was to begin circulating the buffer between the buffer tank and the spinner flask. The inlet and outlet flow rates were balanced to maintain a constant level of buffer in the flask (approx. 800 mL).
   2. When the recirculating rate was balanced the power supply to the ultrasonic nozzle was activated and set to 6 to 6.5 watts.
   3. The SP-C lipid solution was pumped to the atomizing nozzle at a rate of about 3.0 mL/sec. At this point the buffer flow rate was readjusted to maintain a solution level of 800 mL in the spinner flask.
   4. On completion of spraying the first solution onto the second solution, all solution was collected into the buffer tank and cooled to room temperature. Any necessary overnight or other storage was accomplished by cooling and storing at 2°–8° C.
  F. Ultrafiltration and diafiltration:
   1. The UF/DF of the liposome solution was accomplished via tangential flow filtration. The filter and assembly were first washed with sterile succinate buffer to remove any debris generated during autoclaving. Once clean, the filtration system was subjected to integrity testing to ensure that the membrane(s) were integral and that the assembly was leak free.
   2. Ultrafiltration of the liposome solution was done until a 30 fold concentration was reached.

3. The liposome concentrate was washed with six diavolumes of buffer.

G. Lyophilization:

1. 10 mL glass vials were filled with 5 mL of liposome concentrate. The target composition of the fill is 150 mg of phospholipid and 7.5 mg of SP-C per vial.
2. The lyophilization cycle was:
   a. Freeze from 5° C.–55° C. in 2 hrs
   b. Freeze at –55° C. for 4 hrs
   c. Primary dry ramp from –55° C. to –15° C. in 4 hrs at 70 μm Hg $N_2$
   d. Primary dry at –15° C. and 70 μm Hg $N_2$ for 24 hrs at 70 μm Hg $N_2$
   e. Secondary dry ramp from –15° C. to +25° C. in 4 hrs at 70 μm Hg $N_2$
   f. Secondary dry at +25° C. and 70 μm Hg $N_2$ for 15 hrs
   g. Stopper at 700 mm Hg $N_2$
   Products prepared using this cycle were consistently white to slightly off-white solid cakes. Reconstitution of this product using sterile water for injection (SWFI) provided a stable liposome suspension.

II. Liposome Analysis

Several analyses of the liposome suspension after lyophilization were made. The residual moisture was determined in the dry lyophilized cake. Next, the product was resuspended in either water or saline. A particle size analysis was then done (described below), followed by thermal analysis (data not shown). In additional experiments (not shown), the surfactant characteristics of the liposomes were measured in surface balance (tension) assays with good result.

A. Residual Moisture:

The residual moisture averaged in the 2.5–3% range for the lyophilized SP-C liposome cake prepared by the standard lyophilization cycle just described. An alternate cycle (Primary Drying at –24° C., 320 μm Hg for 14 hrs), performed with a lower shelf temperature and high chamber pressure, produced a cake with moisture in the 4% range. Liposome products produced with both cycles performed well in both in vivo and in vitro surfactant function tests. The lyophilization cycle chosen above is considered more conservative with a lower product temperature of –33° C. during initial primary drying, but longer (12 hrs) than the alternate cycle that has a product temperature of –25° C.

B. Particle Size Analysis:

Reconstitution of the lyophilized SP-C liposome cake using SWFI water provided a stable liposome suspension. The particle size of the liposomes was determined in two ways, by the Brinkman 2010 which uses laser interference, and by the Nicomp 200 which uses laser light scattering. The Brinkman 2010 can resolve particle populations in the 5–100 μm range, while the Nicomp 200 can resolve in the 5–5000 nm range.

The Brinkman gives a result for the number, area, and volume or weight (ellipsoid) average particle size. The number average results show a distribution that is cut off at 1 μm, so it is of questionable value. The weight average results show a distribution in the 20–50 μm range, depending on whether or not the suspension has been lyophilized. The particles here were primarily aggregates when observed by light microscopy. The lyophilized batch is in the smaller, 20 μm range, which was shown superior surface activity in surfactant function tests compared to the non-lyophilized material of the same batch.

The Nicomp 200 resolved two major size populations using its model for normal distribution. Although the liposome suspension was likely to be non-normal, it was Close enough to get quantitative results from this method. The results obtained here were consistent with earlier studies of lung surfactant using electron microscopy and Coulter counter techniques, which also found two populations in similar size ranges. The first distribution was in the 50 nm range and the second in the 2 μm range. The larger population was absent for non-lyophilized samples, which might be a clue to their lower biological activity.

A liposome size analysis of liposomes produced at varying nozzle frequency and temperature in the spray step is shown in Table 1 below.

TABLE 1

LIPOSOME SIZE ANALYSIS

| SAMPLE | mg/ml SP-C | NOZZLE FREQUENCY (kHz)[5] | PROCESS TEMP. (°C.) | LIPOSOME SIZE AFTER CAKE RECONSTITUTION | | |
|---|---|---|---|---|---|---|
| | | | | Size by LI Aggregate DV (μm)[1] | Size by DLLS[4] (nm) (two populations) | |
| CONTROL[2] | 0.5 | | | 63[3] | 1350 | 50 |
| 19-4 | 0.5 | 120 | 65 | 61 | 1490 | 62 |
| 19-3 | 0.5 | 120 | 20 | 71 | 1380 | 36 |
| 19-5 | 1.0 | 48 | 20 | 54 | 2540 | 11 |
| 19-7 | 0.5 | 48 | 20 | 68 | 2230 | 51 |
| 19-8 | 0.5 | 48 | 65 | 56 | 1720 | 70 |

[1]Determined by laser interferency (Brinkman 2010).
[2]Prepared by nitrogen blowing method (SP-C dissolved in IPA was placed in a vial; $N_2$ was blown into the vial, blowing out the alcohol and leaving a thin film which was reconstituted to form the control liposomes).
[3]20:1 dilution of reconstituted solution.
[4]Dynamic laser light scattering (Nicomp 200).
[5]Using a SONO-TEK Series 8700-120 nozzle.

We claim:

1. A method for the preparation of liposomes for delivering a biologically active polypeptide to a patient, comprising:
   a) solubilizing an amphipathic liposome-forming material in a pharmaceutically acceptable organic solvent which is readily miscible in a buffer solution thereby forming a first formulation, wherein the first formulation further comprises said biologically active polypeptide;
   b) without added pressurization, spraying the first formulation through a frequency-generated vibrated atomization nozzle onto the surface of an aqueous buffer solution such that said solvent is diluted in said buffer solution and liposomes form within said buffer solution, wherein the size of the liposomes is altered by changing the nozzle frequency; and c) removing the solvent from the liposomes.

2. The method of claim 1 wherein said spraying step b) is performed in a spray chamber, wherein the inside of the spray chamber is at atmospheric pressure during said spraying step.

3. The method of claim 1 wherein the amphipathic material comprises a surfactant.

4. The method of claim 1 wherein the polypeptide is soluble in the solvent and is able to be retained within the liposomes or be associated with the amphipathic material forming the liposomes.

5. The method of claim 1 wherein the buffer solution is pharmaceutically acceptable.

6. The method of claim 5 wherein the pharmaceutically acceptable buffer solution comprises a succinate buffer.

7. The method of claim 1 wherein the first formulation and the buffer solution are kept at a temperature of 20°–80° C.

8. The method of claim 1 wherein the polypeptide is selected from the group consisting of: glycoprotein, lipoprotein, receptor, growth factor, adhesion molecule, hormone, neurotransmitter, tumorocidal agent, toxin, enzyme, and immunoglobulin.

9. The method of claim 1 wherein the polypeptide comprises Lung Surfactant Protein C.

10. The method of claim 1 wherein the solvent is removed from the liposome suspension by diafiltration.

11. The method of claim 1 comprising the additional step of sterilizing one or more of the recovered liposome, the buffer solution, or the first formulation.

12. The method of claim 11, wherein said sterilization is accomplished by heat or sterile filtration.

13. The method of claim 1 comprising sterilizing the first formulation and buffer solution prior to step b).

14. The method of claim 13 wherein the sterilization is accomplished by sterile filtration.

15. The method of claim 1 wherein the polypeptide is a lung surfactant protein.

16. The method of claim 1 wherein the liposome is used to deliver the polypeptide to the lungs of the patient.

17. The method of claim 16 wherein the patient has, or is at risk of having, respiratory distress.

18. The method of claim 1 wherein the polypeptide is lipophilic.

19. The method of claim 1 wherein the first formulation and buffer solution are provided at the same temperature throughout the method.

20. The method of claim 1 comprising heating the first formulation and buffer solution prior to step b).

21. The method of claims 20 wherein the first formulation and buffer solution are heated to a temperature between about 45°–75° C.

22. The method of claim 21 wherein the first formulation and buffer solution are heated to a temperature between about 55°–65° C.

23. The method of claim 1 wherein the organic solvent is a low molecular weight alcohol.

24. The method of claim 1 wherein the solvent consists essentially of alcohol.

25. The method of claim 23 wherein the alcohol is isopropyl alcohol.

26. The method of claim 1 further comprising concentrating the liposomes after step c).

27. The method of claim 26 wherein the liposomes are concentrated using ultrafiltration.

28. The method of claim 27 further comprising lyophilizing the concentrated liposomes.

* * * * *